United States Patent [19]

Braun

[11] Patent Number: 4,533,246
[45] Date of Patent: Aug. 6, 1985

[54] PHOTOMETER FOR MEASURING ATOMIC FLUORESCENCE

[75] Inventor: Klaus Braun, Uberlingen, Fed. Rep. of Germany

[73] Assignee: Bodenseewerk Perkin-Elmer & Co., GmbH, Uberlingen, Fed. Rep. of Germany

[21] Appl. No.: 482,086

[22] Filed: Apr. 4, 1983

[30] Foreign Application Priority Data

Apr. 23, 1982 [DE] Fed. Rep. of Germany ....... 3215249

[51] Int. Cl.³ ............................................. G01N 21/64
[52] U.S. Cl. .................................. 356/317; 250/458.1
[58] Field of Search ................. 356/73, 311, 312, 315, 356/316, 317, 318, 323, 325, 417; 250/458.1, 459.1, 461.1, 461.2, 365, 372, 373

[56] References Cited

U.S. PATENT DOCUMENTS

| | | |
|---|---|---|
| 2,494,440 | 1/1950 | Haynes ................................. 356/325 |
| 3,297,873 | 1/1967 | Hovnanian et al. ................. 250/372 |
| 3,520,614 | 7/1970 | Goldstein ............................ 356/325 |
| 3,811,777 | 5/1974 | Chance ................................ 356/318 |
| 3,822,941 | 7/1974 | Roche et al. ........................ 356/325 |
| 3,920,334 | 11/1975 | Steichen et al. ..................... 356/73 |
| 4,099,872 | 7/1978 | White .................................. 356/325 |

FOREIGN PATENT DOCUMENTS

| | | |
|---|---|---|
| 1291533 | 3/1969 | Fed. Rep. of Germany . |
| 2656417 | 7/1977 | Fed. Rep. of Germany . |
| 3001053 | 7/1981 | Fed. Rep. of Germany . |
| 2239170 | 2/1975 | France .................................. 356/73 |

OTHER PUBLICATIONS

"Spectrum Analyzer," R. W. Kern, IBM Technical Disclosure Bulletin, vol. 18, No. 9, Feb. 1976, p. 2845.

*Primary Examiner*—F. L. Evans
*Assistant Examiner*—Joel L. Harringa
*Attorney, Agent, or Firm*—E. T. Grimes; J. D. Crane

[57] ABSTRACT

In a photometer for measuring atomic fluorescence, a partial light beam is branched off the exciting light beam by means of a mirror having a hole. The partial light beam falls on a scattering disc, from which a reference light beam impinges upon the detector through opposite windows of the measuring cell. A chopper alternately transmits the exciting light beam and the partial light beam. The signal thus obtained at the detector permits compensation of the influence of variations of the light source brightness and of contamination of the windows.

7 Claims, 1 Drawing Figure

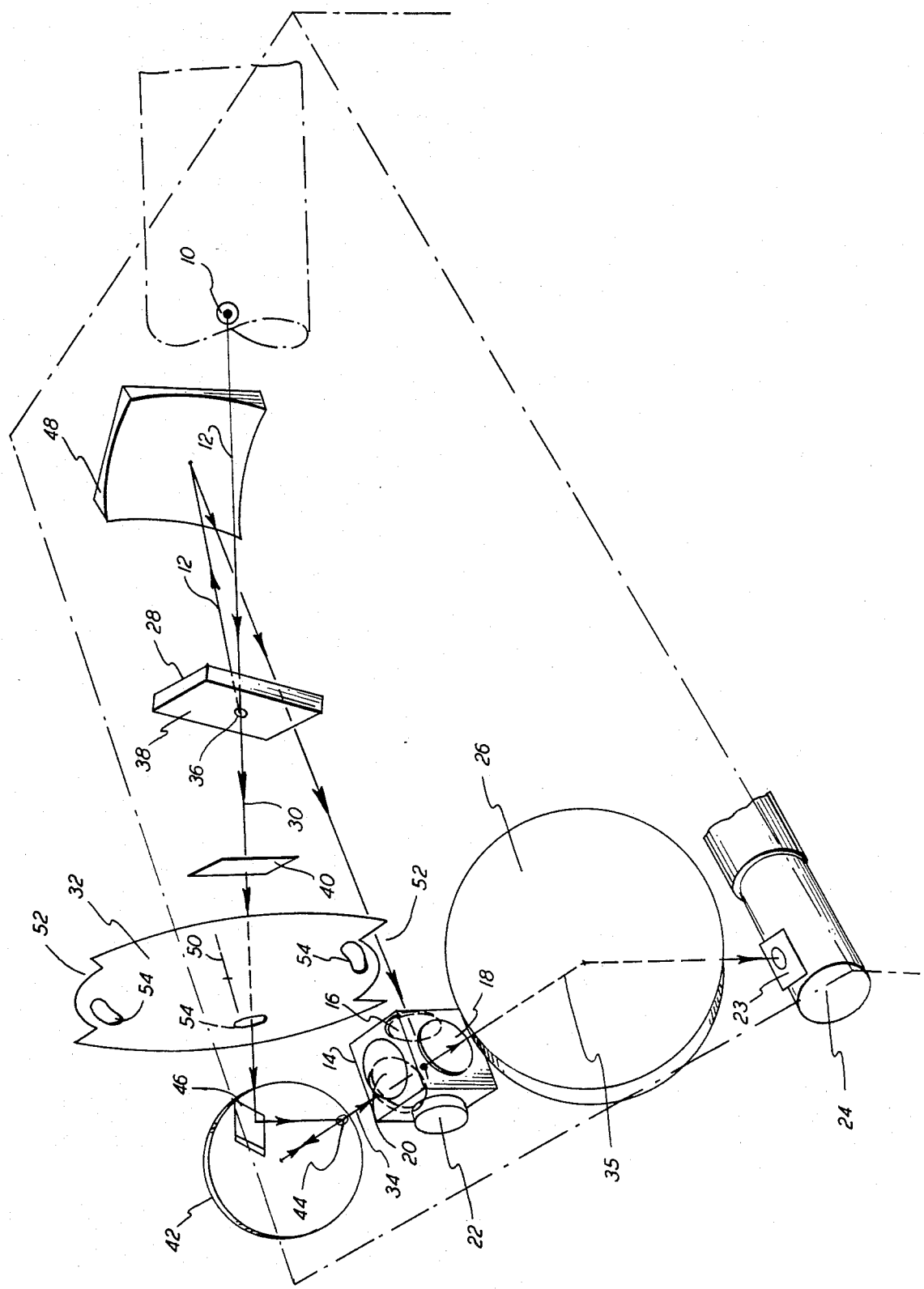

PHOTOMETER FOR MEASURING ATOMIC FLUORESCENCE

BACKGROUND OF THE INVENTION

The present invention generally relates to a photometer for measuring atomic fluorescence and, in particular, relates to such a photometer having means for compensating for lamp or window errors.

A conventional photometer is described in the German Offenlegungsschrift No. 30 01 053. In this prior art arrangement, a heated dissociation device is connected to the measuring cell, in which dissociation device volatile hydrides of a sought element which are gained from a sample solution by adding reagent, are flamelessly thermally decomposed. The free atoms thus developing in the heated dissociation device enter the measuring cell and are excited to atomic fluorescence by an exciting light beam. The measuring cell is substantially cubic and includes a window for the exciting light beam to enter as well as two windows on diametrically opposite sides. The fluorescence radiation is detected by means of a photoelectric detector through one window. In general, a concave mirror is disposed in front of the opposite window, which concave mirror reflects the fluorescence radiation emerged into this direction back to the detector.

Preferably, spectral lamps having electrodeless discharge are used for exciting atomic fluorescence. These spectral lamps suffer from the disadvantage that the radiation density thereof is often unstable or stabilizes only after a long working period. A further problem exists in that the windows of the measuring cell are often contaminated by decomposition products of the sample. This also results in errors.

Double-beam spectrophotometers are known in which a measuring and a reference light beam are alternately directed to a photoelectric detector by a suitable chopper. The measuring light beam passes through a measuring cell and the reference light beam passes through a reference cell which may also contain pure solvent, for example. The influence of variation of lamp brightness and the influence of the cell can be compensated for by processing the electric signals detected at the detector.

In the prior art double-beam spectrophotometers, a measuring and reference light beam emanating from a light source immediately impinged upon the photoelectric detector. These prior art structures are therefore not suitable for photometers measuring atomic fluorescence. Particularly, it would not be possible using the techniques of usual doublebeam spectrophotometers to compensate for errors resulting from contamination of the windows of the measuring cell by decomposition products of the sample.

SUMMARY OF THE INVENTION

Accordingly, it is one object of the invention to provide a photometer for measuring atomic fluorescence such that a reference signal is generated to permit compensation of variation of lamp brightness and/or of the contamination of the windows of the measuring cell.

This object is achieved, at least in part, by a photometer the optical system of which comprises a beam splitter by means of which a partial light beam for generating a reference light beam can be branched off the exciting beam, a chopper arranged to differently modulate the exciting light beam and the partial light beam whereby radiation of the partial light beam as a reference light beam impinges upon the photoelectric detector through the third window, the measuring cell and the second window.

BRIEF DESCRIPTION OF THE DRAWING

An embodiment of the invention is described in greater detail hereinbelow with reference to the accompanying drawing, the single FIGURE of which is a schematic perspective of an optical arrangement of a photometer embodying the principles of the present invention.

DETAILED DESCRIPTION OF THE INVENTION

A photometer for measuring atomic fluorescence and embodying the principles of the present invention includes a light source 10 and an optical system for generating an exciting light beam 12 emanating from the light source 10. A measuring cell 14 has a first window 16 through which the exciting light beam 12 enters the measuring cell 14, more fully described hereinafter. The measuring cell 14 has a second window 18 through which fluorescence radiation, transverse to the direction of the exciting light beam 12, can be detected. A third window 20 is located opposite the second window 18. In practice, there may be a cuboid measuring cell 14 having the first window 16 on one side and having the windows 18 and 20 on two opposite sides adjacent thereto. A light trap 22 is disposed opposite the window 16, which light trap completely absorbs the exciting light beam entering the measuring cell 14. Thereby, vagabond radiation is substantially completely avoided which might otherwise disturb the measuring as an undesired stray light. A photoelectric detector 24 is impinged upon by radiation emerging through the second window 18, through a toroidal mirror 26.

A "cloud of atoms" is formed in the measuring cell 14, which "cloud of atoms" contains an element sought in the sample, in its atomic state. The atoms are excited by the radiation of the exciting light beam. When returning into their ground state, they emit fluorescence radiation uniformly radiating to all sides and detected by the photoelectric detector 24 through the window 18. The signal of the detector 24, however, is not only dependent on the quantity of atoms in the measuring cell 14, but also on the brightness of the light source 10 and on the transparence of the windows 16 and 18. The errors resulting therefrom are to be compensated.

To this end, the optical system for generating the exciting light beam 12 comprises a beam splitter 28, by which a partial light beam 30 may be branched off the exciting light beam 12 for generating a reference light beam. A chopper 32 is provided, which is arranged to modulate the exciting light beam 12 and the partial light beam 30 differently. Radiation of the partial light beam 30 impinges upon the photoelectric detector 24 as a reference light beam 34 which passes through the third window 20, the measuring cell 14 and the second window 18. As the partial light beam 30 and thus the reference light beam 34 emanate from the same light source 10 as the exciting light beam 12, the reference light beam varies to the same extent as the exciting light beam, if the brightness of the light source 10 varies. Thus, the reference light beam 34 generates a detector signal at the detector 24, which detector signal, for example, may be automatically controlled to a constant value, whereby the influence of variations of the lamp brightness on the useful signal from the fluorescence radiation (automatically controlled as well) are compensated for. The reference light beam 34 passes through two windows of the measuring cell 14, namely the third window 20 and the second window 18. The light flux of the reference light beam 34 impinging upon the photoelectric detector 24 thus is a square function of an attenuation factor caused by contamination of the windows 20 and 18, respectively. The fluorescence radiation is also a square function of this attenuation factor. On one hand, the exciting light beam 12 is attenuated through the first window 16 by this attenuation factor. On the other hand, the fluorescence radiation emerging through the second window 18 is also attenuated by this factor. If, therefore, a compensation of the variation of the light beam is effected by the reference light beam 34 and the signal resulting therefrom, the useful signal is then also compensated for with respect to the attenuation due to contamination of the windows 16 and 18. It is presupposed that contamination occurs on all three windows 16, 18 and 20 to the same extent, which can be presupposed with contamination due to condensation of sample components.

The beam splitter 28 comprises a mirror 38 provided with a hole 36, the exciting light beam 12 being reflected by the mirror and the partial light beam 30 passing through the hole. The hole 36 is, preferably, only very small compared to the cross sectional area of the exciting light beam 12. Therefore, only a small light flux of the exciting light beam 12 is branched off through the hole 36 as a partial light beam 30. A spectrally neutral attenuator 40 is disposed in the path of rays of the partial light beam 30. This attenuator 40 may, for example, be a perforated foil or a grid.

A concave mirror 42 is disposed on the side of the measuring cell 14 opposite the detector 24 and facing the third window 20. The concave mirror 42 reflects the fluorescence radiation emerging through the third window 20 back to the measuring cell 14 and the detector 24. It increases therefore the yield of fluorescence radiation detected by the detector 24. Beam combining means 44 are disposed between the concave mirror 42 and the third window 20, said beam combining means covering only a small portion of the aperture angle of the concave mirror 42, and the partial light beam 30 being directed thereon by means of a deflecting mirror 46 for generating the reference light beam 34 through the measuring cell 14 upon the detector 24. In the preferred embodiment illustrated, the beam combining means 44 are formed by a scattering disc.

The exciting light beam 12 reflected by the mirror 38 of the beam splitter 28 impinges upon a concave mirror 48 reflecting the exciting light beam 12 and focusing it through the first window 16 of the measuring cell 14. The beam chopper 32 is a chopper disc rotating about an axis of rotation 50, which chopper disc is disposed in the paths of rays of the partial light beam 30 and the exciting light beam 12. Said light beams 30, 12 fall on the chopper disk in areas having different radial distances from the axis of rotation 50. The exciting light beam 12 falls on the edge of the chopper disc, whereas the partial light beam 30 falls on the chopper disc in an area located nearer to the axis of rotation 50. In these areas, the chopper disc has sections 52 or apertures 54 to permit the passage of the exciting light beam 12 and the partial light beam 30, respectively, out of phase.

The embodiment described operates as follows.

The fluorescence radiation detected through the second window 18 is rather weak compared to the exciting light beam 12. Correspondingly, the reference light beam 34 should also be attenuated considerably compared to the exciting light beam 12. On one hand, this occurs due to the fact that only a small portion of the cross-sectional area of the exciting light beam 12 passes through the hole 36 as a partial light beam 30. This partial light beam 30 is attenuated once more in well-defined manner by means of the attenuator 40. The partial light beam 30 then falls on the scattering disc 44 serving as beam combining means 44. Part of the radiation from this scattering disc impinges upon the detector 24 through window 20 and window 18 as reference radiation. The scattering disc does not virtually affect the fluorescence radiation reflected from the mirror 42 to the measuring cell 14. Exciting light beam 12 and reference light beam 30 are alternately transmitted by the chopper 32. The aperture 54 shown in dashed lines in the area of the partial light beam 30 shows that exciting light beam 12 and partial light beam 30 are transmitted by the chopper 32 with a 90° phase shift. The exciting light beam 12 enters the measuring cell 14 through the window 16 and is completely absorbed by the light trap 22. Fluorescence radiation is generated by the exciting light beam 12, and is detected by the photoelectric detector 24 through the second window 18. The light flux impinging upon the photoelectric detector 24, on one hand, depends on the brightness of the light source 10 and, on the other hand, is a square function of the attenuation by the windows 16 and 18 affecting, on one hand, the exciting light beam 12 and, on the other hand, the fluorescence radiation, respectively. Additionally, the light flux is, of course, a measure of the quantity of the sought atoms in the measuring cell 14. The reference light beam 34 passes through the third window 20 and the second window 18 of the measuring cell 14 and impinges also upon the photoelectric detector 24 with a phase shift. The light flux impinging from the reference light beam upon the photoelectric detector 24 also depends on the brightness of the lamp and is also a square function of the attenuation of the light beam through the windows 20 and 18. If, therefore, the signal of the detector 24 is automatically controlled such that the signal component generated by the reference light beam 34 has a constant amplitude, then the influence above described is also compensated for in the signal component generated by the fluorescence radiation.

Although the above description is directed to a preferred exemplary embodiment, it is not intended to be so limiting. Thus, it is understood that other embodiments and arrangements can be made which do not depart from the scope and spirit hereof. Thus, the present invention is deemed limited by the appended claims and the reasonable interpretation thereof.

What is claimed is:

1. Photometer for measuring atomic fluorescence, comprising:
   a light source;
   an optical system for generating an exciting light beam emanating from said light source; said optical system including a beam splitter, by means of which a partial light beam can be branched off said exciting light beam;
   a measuring cell, said measuring cell including a first window through which said exciting light beam enters said measuring cell, a second window through which fluorescence radiation transverse to the direction of said exciting light beam can be detected and a third window disposed opposite said second window;

said optical system including means to direct said exciting light beam through said first window and means to direct said partial light beam through said third window in a direction transverse to the direction said exciting light beam enters said cell through said first window;

a photoelectric detector arranged such that the fluorescence radiation and said partial light beam emerging through said second window impinges thereon;

said optical system further including means to reflect fluorescence radiation emerging through said third window back through said third window and into said cell in a direction toward said detector;

a chopper positioned to differently modulate said exciting light beam and said partial light beam.

2. Photometer as claimed in claim 1 wherein:

said beam splitter is a mirror provided with a hole, said exciting light beam being reflected by said mirror, and said partial light beam passing through the said hole.

3. Photometer as claimed in claim 2 wherein:

a spectrally neutral attenuator is disposed in the path of rays of said partial light beam.

4. Photometer as claimed in claim 2 wherein:

said exciting light beam reflected by said mirror of said beam splitter impinges upon a concave mirror reflecting said exciting light beam and focusing it upon a spot inside said measuring cell through the first window thereof; and said beam interrupter is a chopper disc rotating around an axis of rotation which is disposed in the paths of rays of said partial light beam and said exciting light beam, which chopper is impinged upon by said light beams in areas having different radial distances from said axis of rotation; and means within said areas for transmitting said exciting light beam and said partial light beam out of phase.

5. Photometer as claimed in claim 1 wherein:

said means to reflect fluorescence radiation comprises a concave mirror disposed on the side of said measuring cell opposite said detector and facing said third window which concave mirror reflects fluorescence radiation emerging through said third window back to said measuring cell and said detector;

said means to direct said partial light beam through said third window includes beam combining means disposed between said concave mirror and said third window, said beam combining means covering only a small portion of the aperture angle of said concave mirror, said partial light beam being directed thereon.

6. Photometer as claimed in claim 5 wherein:

said beam combining means includes a scattering disc.

7. The photometer of claim 1 additional including a light trap disposed opposite said first window to absorb said exciting light beam.

* * * * *